United States Patent [19]

Häusler et al.

[11] Patent Number: 5,057,521
[45] Date of Patent: Oct. 15, 1991

[54] USE OF BICYCLIC IMIDAZOLE COMPOUNDS FOR THE TREATMENT OF HYPERALDOSTERONISM

[75] Inventors: Albert Häusler, Muttenz; Ajay Bhatnagar, Basel, both of Switzerland

[73] Assignee: Ciba-Geigy Corporation, Ardsley, N.Y.

[21] Appl. No.: 412,369

[22] Filed: Sep. 26, 1989

[30] Foreign Application Priority Data

Oct. 26, 1988 [CH] Switzerland ............... 3994/88

[51] Int. Cl.$^5$ ............................................. A61K 31/41
[52] U.S. Cl. ................................... 514/300; 514/210; 514/214; 514/227.8; 514/235.8; 514/255; 514/393; 514/413
[58] Field of Search ............... 514/300, 214, 393, 413

[56] References Cited

U.S. PATENT DOCUMENTS

| | | | |
|---|---|---|---|
| 4,588,732 | 5/1986 | Browne | 514/300 |
| 4,617,307 | 10/1986 | Browne | 514/300 |
| 4,728,645 | 3/1988 | Browne | 514/214 |
| 4,889,861 | 12/1989 | Browne | 514/300 |

OTHER PUBLICATIONS

Chemical Abstracts; vol. III (1989), #187280s; Lamberts et al.
Clin. Research 37, No. 2,535A (1989).
Oral presentation of Dr. J. R. Hanagan, 10/6/88, Pretoria, South Africa.
Journal of Clinical Endocrinology and Metabolism, 68, No. 1, 99-106 (1989).
Dose-Related Endocrine Study of Aramatase Inhibitor. Abstract of oral presentation of Dr. Santen at the 70th annual meeting of the Endocrine Society.
J. Endocrinol., 119 (Suppl.) 1988, Abstract 123.

*Primary Examiner*—Johann Richter
*Attorney, Agent, or Firm*—Irving M. Fishman

[57] ABSTRACT

The invention relates to specific bicyclic imidazole compounds such as 5-(p-cyanophenyl)-5,6,7,8-tetrahydroimidazo[1,5-a]pyridine, or pharmaceutically acceptable non-toxic salts thereof, for the treatment of hyperaldosteronism, and to a method of treating hyperaldosteronism using such compounds, as well as to the use of said compounds for the preparation of pharmaceutical compositions for the treatment of hyperaldosteronism.

4 Claims, No Drawings

USE OF BICYCLIC IMIDAZOLE COMPOUNDS FOR THE TREATMENT OF HYPERALDOSTERONISM

The present invention relates to the use of bicyclic imidazole compounds for the treatment of hyperaldosteronism, and to the use of bicyclic imidazole compounds for the preparation of pharmaceutical compositions for the treatment of hyperaldosteronism.

Hyperaldosteronism is a term signifying diseases which are characterised by an increased level of aldosterone. These diseases may have their origin in an increased production of aldosterone (primary hyperaldosteronism, Conn's syndrome) or may also have other causes (secondary hyperaldosteronism). Such diseases may occur not only in association with, but also without, high blood pressure (hypertension) and its clinical symptoms or organic lesions caused thereby. Furthermore, such diseases may occur in association with, and also without, loss of electrolyte and the concomitant symptoms, as well as with, and also without, alkalosis and the paraesthesia and tetany caused thereby, and also with and without hypernatraemia.

In particular, the following symptoms are observed in patients with primary hyperaldosteronism according to Conn (evaluation of 145 cases), from Stegglin and Siegenthaler, Differentialdiagnose innerer Krankheiten, Thieme, Stuttgart 1980 (frequency indicated in brackets): hypertension (100%), hypokalaemia (90%), proteinuria (85%), hyposthenuria (80%), ECG changes (80%), myasthenia (73%), polyuria (72%), hypernatraemia (65%), headaches (51%), retinopathy (50%), polydipsia (46%), cardiomegalia (41%), paraesthesia (24%), impaired vision (21%), intermittent paralysis (21%), and intermittent tetany (21%).

European patent application 0 165 904 discloses bicyclic imidazole compounds of formula I

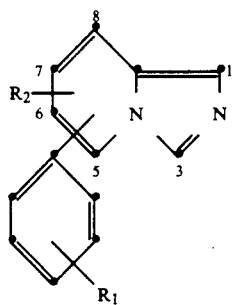

wherein $R_1$ is hydrogen, lower alkyl, substituted lower alkyl, nitro, halogen, free, etherified or esterified hydroxy, free, etherified, oxidised-etherified or esterified mercapto, unsubstituted amino or mono-or disubstituted amino, ammonio, free or functionally modified sulfo, free or functionally modified formyl, $C_2$-$C_{20}$acyl or free or functionally modified carboxy; and $R_2$ is hydrogen, lower alkyl, substituted lower alkyl, halogen; free, etherified or esterified hydroxy; free, etherified, oxidised-etherified or esterified mercapto; free or functionally modified carboxy or acyl; and the 7,8-dihydro derivatives thereof; and also compounds of formula I*

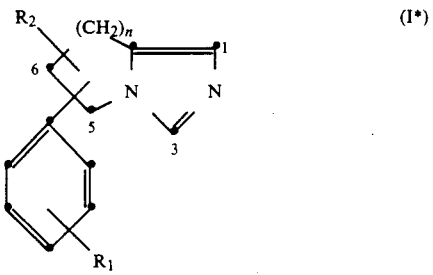

wherein n is 0, 1, 2, 3 or 4, and $R_1$ and $R_2$ are as defined for formula I; in a compound of formula I* it being possible for the two substituents $C_6H_4$—$R_1$ and $R_2$ to be attached to each of the saturated carbon atoms of the saturated ring, either both to the same carbon atom or both to different carbon atoms; and stereoisomers, mixtures of stereoisomers and pharmaceutically acceptable salts thereof.

It is claimed in this patent specification that the compounds inhibit aromatase and can therefore be used for the treatment of diseases which respond to aromatase inhibition. As such diseases, mention is made of gynaecomastia and oestrogen-dependent diseases including oestrogen-dependent breast cancer.

It is also known, for example, from European patent application 0 114 573 that some of the compounds of formulae I and I* also inhibit thromboxane synthetase and are therefore suitable for the treatment of diseases which respond to an inhibition of thromboxane synthetase such as cardiovascular diseases, for example thrombo-embolism.

It has now been found that the compounds of formulae I and I*, wherein $R_1$, $R_2$ and n are as defined above, and the pharmaceutically acceptable non-toxic salts thereof, inhibit aldosterone secretion in mammals including humans, and can therefore be used for the treatment of hyperaldosteronism.

Pharmaceutically acceptable non-toxic acid addition salts are in particular those with suitable inorganic or organic acids, for example strong mineral acids such as hydrochloric acid, sulfuric acid or phosphoric acid, or with organic acids, especially aliphatic or aromatic carboxylic or sulfonic acids, for example formic acid, acetic acid, propionic acid, succinic acid, glycolic acid, lactic acid, hydroxysuccinic acid, tartaric acid, citric acid, maleic acid, fumaric acid, hydroxymaleic acid, pyruvic acid, phenylacetic acid, benzoic acid, 4-aminobenzoic acid, anthranilic acid, 4-hydroxybenzoic acid, salicylic acid, 4-aminosalicylic acid, pamoic acid, gluconic acid, nicotinic acid, methanesulfonic acid, ethanesulfonic acid, halobenzenesulfonic acid, p-toluenesulfonic acid, naphthalenesulfonic acid, sulfanilic acid or cyclohexylsulfamic acid; or with other acid organic compounds such as ascorbic acid. Pharmaceutically acceptable salts may also be formed, for example, with amino acids such as arginine or lysine.

Compounds of this invention which contain acid groups, for example a free carboxyl or sulfo group, can also form pharmaceutically acceptable metal or ammonium salts such as alkali metal salts or alkaline earth metal salts, for example sodium, potassium, magnesium or calcium salts, and also ammonium salts which are derived from ammonia or suitable organic amines. Suitable amines are, in particular, aliphatic, cycloaliphatic, cycloaliphatic-aliphatic or araliphatic primary, secondary or tertiary mono-, di- or polyamines such as lower alkylamines, for example diethylamine or triethylamine, hydroxy-lower alkylamines, for example 2-hydroxyethylamine, bis(2-hydroxyethyl)amine or tris(2-hydroxyethyl)amine, basic aliphatic esters of carboxylic acids, for example 2-diethylaminoethyl 4-aminobenzoate, lower alkyleneamines, for example 1-ethylpiperidine, cycloalkylamines, for example dicyclohexylamine, benzylamines, for example N,N'-dibenzylethylenediamine; and also heterocyclic bases, for example of the pyridine type such as pyridine, collidine or quinoline.

Mono- or polysalts can be formed if the compounds of the invention contain several acid or basic groups. Those compounds which contain an acid and a basic group can also be obtained in the form of inner salts, i.e. as zwitter ions, or a part of the molecule can be in the form of an inner salt and another part of the molecule in that of a normal salt.

The inhibitory action of the compounds of formulae I and I* on aldosterone secretion is determined, for example, by means of the following experimental methods:

1. In vitro method for determining the inhibition of ACTH-induced aldosterone production in the adrenals of rats or mice (ACTH=adrenocorticotropic hormone): adult male rats (200-300 g) or mice (25-35 g) are decapitated, the adrenals are removed, and each gland is divided into 8 fragments of equal size. An equal number of fragments are incubated for 2 hours at 37° C. in each of a number of flasks containing a suitable buffer solution (Krebs-Ringer bicarbonate buffer, pH 7.4) with the addition of ACTH without test compound (control value) and with different concentrations of test compound. After incubation, the incubation medium is separated from any pieces of tissue by centrifugation. The aldosterone content of the incubation medium is measured by means of a specific radioimmuno assay, and expressed as aldosterone production per 2 hours. The inhibitory action of the test compounds is expressed in a reduction of aldosterone production per 2 hours and is indicated in percent (of the control value). The compounds of formula I effect a reduction of aldosterone production from a concentration of ca. 0.1 µM (=100 nM).

2. The compounds of formulae I and I* inhibit very effectively, i.e. even at a concentration of ca. 100 nM or at still lower concentrations, the aldosterone excretion, stimulated by angiotensin II, of adrenocortical cells which are prepared from an adrenoma of a patient suffering from Conn's syndrome (=primary hyperaldosteronism).

Hence the present invention relates to the use of the compounds of formulae I and I*, wherein $R_1$, $R_2$ and n have the meanings as defined above, and of the pharmaceutically acceptable non-toxic salts thereof, for the treatment of hyperaldosteronism, namely in daily doses of ca. 5 mg to 30 mg, based on an individual of ca. 70 kg body weight, the individual doses administered being from ca. 2 to 20 mg.

The invention further relates to a method of treating hyperaldosteronism using compounds of formula I or I* respectively, wherein $R_1$, $R_2$ and n have the meanings as defined above, and the pharmaceutically acceptable non-toxic salts thereof, as well as to the use of said compounds for the preparation of pharmaceutical compositions for the treatment of hyperaldosteronism.

The general terms used throughout this specification for defining the compounds of formulae I and I* have the following meanings.

Organic radicals qualified by the term "lower" normally contain up to 7 carbon atoms inclusive, preferably up to 4 carbon atoms inclusive.

The compounds of formula I*, as well as specific 7,8-dihydro derivatives of the formula I, contain at least one asymmetrical carbon atom. They may occur as R- or S-enantiomers as well as enantiomeric mixtures thereof, for example as racemate. Formulae I and I* comprise all these forms, also all further isomers and mixtures of at least two isomers, for example mixtures of diastereoisomers or mixtures of enantiomers, which may then result if one or more further centres of asymmetry are present in the molecule.

Lower alkyl is typically n-propyl, isopropyl, n-butyl, sec-butyl or tert-butyl, and also n-pentyl, isopentyl, neopentyl, n-hexyl, isohexyl or n-heptyl, but is preferably ethyl and, most preferably, methyl.

Substituted lower alkyl $R_1$ is preferably substituted by hydroxy, etherified hydroxy, for example lower alkoxy, esterified hydroxy, for example lower alkanoyloxy, acyl, for example lower alkanoyl, amino, mono- or disubstituted amino, for example lower alkylamino or di-lower alkylamino, halogen, preferably fluoro, free or functionally modified sulfo, preferably sulfo, or free or functionally modified carboxy, for example carboxy, lower alkoxycarbonyl, carbamoyl or cyano.

Substituted lower alkyl $R_2$ is preferably substituted by aryl or free or functionally modified carboxy, preferably carboxy or lower alkoxycarbonyl.

Halogen is typically bromo or iodo, preferably fluoro and, most preferably, chloro.

Etherified hydroxy is preferably lower alkoxy, and also aryloxy or aryl-lower alkoxy. Esterified hydroxy may be acyloxy, preferably lower alkanoyloxy, but may also be aroyloxy or lower alkoxycarbonyloxy.

Etherified mercapto is preferably lower alkylthio, but may also be arylthio or aryl-lower alkylthio. Oxidised-etherified mercapto may be arylsulfinyl or arylsulfonyl, and is preferably lower alkylsulfinyl or lower alkylsulfonyl. Esterified mercapto may be acylthio such as lower alkanoylthio.

Mono-substituted amino is preferably lower alkylamino, and may also be arylamino, aryl-lower alkylamino or acylamino, preferably lower alkanoylamino, but may also be aroylamino.

Disubstituted amino is preferably di-lower alkylamino, and may also be lower alkyleneamino, oxa-, thia- or aza-lower alkyleneamino, in which last mentioned radical the aza-nitrogen atom may be substituted by, for example, a hydrocarbon radical such as lower alkyl. Exemplary of these radicals are N-morpholino, N-thiomorpholino or N-piperazino or N-piperazino which is substituted in 4-position by lower alkyl.

Ammonio comprises, for example, quaternary ammonium salts which are derived from the corresponding above mentioned disubstituted amino groups and which contain, as quaternary substituents, for example unsubstituted or substituted lower alkyl, preferably lower alkyl, hydroxy, halogen or aryl-lower alkyl. Preferably ammonio is tri-lower alkylammonio, for example trimethylammonio. The ammonium salts correspond to the salts defined below, especially the salts which are cited as pharmaceutically acceptable non-toxic acid addition salts, and, most particularly, to the salts which are formed with hydrohalic acids, sulfuric acid or phosphoric acid.

Free or functionally modified sulfo is, for example, sulfo (—SO$_3$H), esterified sulfo, for example lower alkoxysulfonyl, amidated sulfo, for example sulfamoyl, lower alkylsulfamoyl or di-lower alkylsulfamoyl, or is a sulfonyl halide, for example sulfonyl chloride; and is preferably sulfo or sulfamoyl.

Free or functionally modified formyl is preferably formyl or iminomethyl (—CH=NH), which may be substituted at the nitrogen by free, etherified or esterified hydroxy, for example hydroxy, lower alkoxy or lower alkanoyloxy, by lower alkyl, aryl or amino; but may also be, for example, an acetal, for example a di-lower alkyl acetal such as dimethyl acetal.

Acyl, which normally contains 1 to 20 carbon atoms, is the corresponding radical of a carboxylic acid, preferably aroyl or halo(C$_2$-C$_7$)alkanoyl, and is, in particular, lower alkanoyl. C$_1$Alkanoyl corresponds to formyl.

Free or functionally modified carboxy is typically carboxy, esterified carboxy, preferably lower alkoxycarbonyl, amidated carboxy, preferably carbamoyl, lower alkylcarbamoyl, di-lower alkylcarbamoyl or hydroxycarbamoyl, or is cyano. Further, it comprises, for example, heterocyclic derivatives of carboxy, preferably 5-tetrazolyl or unsubstituted or lower alkyl-substituted 4,5-dihydro-2-oxazolyl.

Aryl by itself or as moiety of radicals such as aryloxy, aryl-lower alkylthio, arylsulfonyl, arylamino and the like, may be 1-or 2-naphthyl, preferably phenyl which is substituted, preferably monosubstituted, for example by lower alkyl, lower alkoxy and/or halogen and, most preferably, is phenyl.

Aroyl by itself or as moiety of radicals such as aroyloxy and the like is arylcarbonyl, preferably benzoyl.

Lower alkoxy is preferably methoxy or ethoxy, and also n-propoxy, isopropoxy, n-butoxy, isobutoxy or tert-butoxy.

Lower alkanoyloxy is, for example, formyloxy, acetoxy, propionyloxy or pivaloyloxy.

Lower alkanoyl is typically formyl, acetyl, propionyl or pivaloyl. Halo(C$_2$-C$_7$)alkanoyl is preferably trifluoroacetyl. Lower alkanoylamino is preferably acetylamino or propionylamino, but may also be, for example, formylamino.

Lower alkoxycarbonyl is preferably methoxycarbonyl or ethoxycarbonyl. Lower alkoxycarbonyloxy is, for example, methoxycarbonyloxy or ethoxycarbonyloxy.

Lower alkylamino is typically methylamino, ethylamino, n-propylamino or isopropylamino. Di-lower alkylamino is typically dimethylamino, ethylmethylamino or diethylamino. Lower alkyleneamino contains, for example, 2 to 7, preferably 4 to 6, ring carbon atoms, and may be N-pyrrolidino or N-piperidino.

Lower alkylthio is typically methylthio, ethylthio, n-propylthio or isopropylthio, while lower alkysulfinyl is, for example, methylsulfinyl; and lower alkylsulfonyl is typically methylsulfonyl or ethysulfonyl. Lower alkanoylthio is preferably formylthio or acetylthio.

Lower alkoxysulfonyl is typically methoxysulfonyl or ethoxysulfonyl. Lower alkylsulfamoyl is, for example, N-methylsulfamoyl or N-ethylsulfamoyl. Di-lower alkylsulfamoyl is, for example, dimethylsulfamoyl or diethylsulfamoyl.

Lower alkylcarbamoyl is typically N-methylcarbamoyl or N-ethylcarbamoyl, and di-lower alkylcarbamoyl is, for example, dimethylcarbamoyl or diethylcarbamoyl.

Preferably the invention relates to the use of compounds of formula I, wherein $R_1$ is hydrogen, lower alkyl, lower alkyl which is substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or cyano; or is nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, N-thiomorpholino, N-piperazino or N-piperazino which is substituted in 4-position by lower alkyl; or is tri-lower alkylammonio, sulfo, lower alkoxysulfonyl, sulfamoyl, lower alkylsulfamoyl, di-lower alkylsulfamoyl, formyl; or is iminomethyl which may be substituted at the nitrogen by hydroxy, lower alkoxy, lower alkanoyloxy, lower alkyl, phenyl or amino; or is C$_2$-C$_7$ alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; of the 7,8-dihydro derivatives thereof, or of the compounds of formula I*, wherein n is 0, 1, 2, 3 or 4, and $R_1$ and $R_2$ are as defined above for formula I, and the phenyl ring in phenylsulfonyloxy, phenyliminomethyl, benzoyl, phenyl-lower alkyl, phenyl-lower alkylthio and phenylthio may be unsubstituted or substituted by lower alkyl, lower alkoxy or halogen; in a compound of formula I* it being possible for the two substituents C$_6$H$_4$—R$_1$ and R$_2$ to be attached to each of the saturated carbon atoms of the saturated ring, either both to the same carbon atom or both to different carbon atoms; and of stereoisomers, mixtures of stereoisomers or pharmaceutically acceptable salts thereof, for the treatment of hyperaldosteronism, and to a method of treating hyperaldosteronism using such compounds, and to the use of said compounds for the preparation of pharmaceutical compositions for the treatment of hyperaldosteronism.

More particularly, the invention relates to the use of compounds of formula I, wherein $R_1$ is lower alkyl, lower alkyl which is substituted by hydroxy, amino, di-lower alkylamino, 1 to 5 fluorine atoms, carboxy, lower alkoxycarbonyl, carbamoyl or cyano; or is nitro, halogen, hydroxy, lower alkoxy, amino, lower alkylamino, di-lower alkylamino, sulfo, sulfamoyl, formyl, iminomethyl, iminomethyl which is substituted at the nitrogen by hydroxy, lower alkoxy, lower alkanoyloxy, lower alkyl or phenyl; or is carboxy, lower alkoxycarbonyl, carbamoyl, lower alkylcarbamoyl, di-lower alkylcarbamoyl or cyano; and $R_2$ is hydrogen, lower alkyl, lower alkoxy or halogen; or of compounds of formula I*, wherein n is 1, 2 or 3, $R_1$ is as defined above for formula I, and $R_2$ is hydrogen, lower alkyl, phenyl-lower alkyl, carboxy-lower alkyl, lower alkoxycarbonyl-lower alkyl, halogen, lower alkoxy, lower alkylthio, phenyl-lower alkylthio, phenylthio, carboxy, lower alkoxycarbonyl or lower alkanoyl; in a compound of formula I* it being possible for the two substituents $C_6H_4$—$R_1$ and $R_2$ to be attached to each of the saturated carbon atoms of the saturated ring, either both to the same carbon atom or both to different carbon atoms; and of stereoisomers, mixtures of stereoisomers or of pharmaceutically acceptable salts thereof, for the treatment of hyperaldosteronism, and to a method of treating hyperaldosteronism using such compounds, and to the use of said compounds for the preparation of pharmaceutical compositions for the treatment of hyperaldosteronism.

Still more particularly, the invention relates to the use of compounds of formula I, wherein $R_1$ is lower alkyl, hydroxy-lower alkyl, halogen, amino, formyl, carboxy, lower alkoxycarbonyl, carbamoyl, N-lower alkylcarbamoyl or cyano; and $R_2$ is hydrogen; or of compounds of formula I*, wherein n is 1, 2 or 3, $R_1$ is as defined above for formula I, and $R_2$ is hydrogen, lower alkylthio, lower alkoxycarbonyl, phenyl-lower alkyl, carboxy-lower alkyl or lower alkoxycarbonyl-lower alkyl; in a compound of formula I* it being possible for the two substituents $C_6H_4$—$R_1$ and $R_2$ to be attached to each of the saturated carbon atoms of the saturated ring, either both to the same carbon atom or both to different carbon atoms; and of stereoisomers, mixtures of stereoisomers or of pharmaceutically acceptable salts thereof, for the treatment of hyperaldosteronism, and to a method of treating hyperaldosteronism using such compounds, and to the use of said compounds for the preparation of pharmaceutical compositions for the treatment of hyperaldosteronism.

Specifically, the invention relates to the use of one of the following compounds
(a) 5-(p-cyanophenyl)imidazo[1,5-a]pyridine,
(b) 5-(p-ethoxycarbonylphenyl)imidazo[1,5-a]pyridine,
(c) 5-(p-carboxyphenyl)imidazo[1,5-a]pyridine,
(d) 5-(p-tert-butylaminocarbonylphenyl)imidazo[1,5-a]pyridine,
(e) 5-(p-ethoxycarbonylphenyl)-5,6,7,8-tetrahydroimidazo[1,5-a]pyridine,
(f) 5-(p-carboxyphenyl)-5,6,7,8-tetrahydroimidazo[1,5-a]pyridine,
(g) 5-(p-carbamoylphenyl)-5,6,7,8-tetrahydroimidazo[1,5-a]-pyridine,
(h) 5-(p-tolyl)-5,6,7,8-tetrahydroimidazo[1,5-a]pyridine,
(i) 5-(p-hydroxymethylphenyl)imidazo[1,5-a]pyridine,
(j) 5-(p-cyanophenyl)-7,8-dihydroimidazo[1,5-a]pyridine,
(k) 5-(p-bromophenyl)-5,6,7,8-tetrahydroimidazo[1,5-a]pyridine,
(l) 5-(p-hydroxymethylphenyl)-5,6,7,8-tetrahydroimidazo[1,5-a]pyridine,
(m) 5-(p-formylphenyl)-5,6,7,8-tetrahydroimidazo[1,5-a]pyridine,
(n) 5-(p-cyanophenyl)-5-methylthio-5,6,7,8-tetrahydroimidazo[1,5-a]pyridine,
(o) 5-(p-cyanophenyl)-5-ethoxycarbonyl-5,6,7,8-tetrahydroimidazo[1,5-a]pyridine,
(p) 5-(p-aminophenyl)-5,6,7,8-tetrahydroimidazo[1,5-a]pyridine,
(q) 5-(p-formylphenyl)imidazo[1,5-a]pyridine,
(r) 5-(p-carbamoylphenyl)imidazo[1,5-a]pyridine,
(s) 5H-5-(4-tert-butylaminocarbonylphenyl)-6,7-dihydropyrrolo[1,2-c]imidazole,
(t) 5H-5-(4-cyanophenyl)-6,7-dihydropyrrolo[1,2-c]imidazole,
(u) 5H-5-(4-cyanophenyl)-6,7,8,9-tetrahydroimidazo[1,5-a]azepine,
(v) 5-(4-cyanophenyl)-6-ethoxycarbonylmethyl-5,6,7,8-tetrahydroimidazo[1,5-a]pyridine,
(w) 5-(4-cyanophenyl)-6-carboxymethyl-5,6,7,8-tetrahydroimidazo[1,5-a]pyridine,
(x) 5-benzyl-5-(4-cyanophenyl)-5,6,7,8-tetrahydroimidazo[1,5-a]pyridine,
(y) 7-(p-cyanophenyl)-5,6,7,8-tetrahydroimidazo[1,5-a]pyridine,
(z) 7-(p-carbamoylphenyl)-5,6,7,8-tetrahydroimidazo[1,5-a]pyridine,
or of a pharmaceutically acceptable non-toxic salt thereof, for the treatment of hyperaldosteronism, and to a method of treating hyperaldosteronism using such compounds, and to the use of said compounds for the preparation of pharmaceutical compositions for the treatment of hyperaldosteronism.

More specifically, the invention relates to the use of 5-(p-cyanophenyl)-5,6,7,8-tetrahydroimidazo[1,5-a]pyridine, or of a pharmaceutically acceptable non-toxic acid addition salt thereof, for the treatment of hyperaldosteronism, and to a method of treating hyperaldosteronism using such compounds, and to the use of said compounds for the preparation of pharmaceutical compositions for the treatment of hyperaldosteronism. The hydrochloride of this compound inhibits ACTH-induced aldosterone production in the adrenals of rats and mice (assay 1) with an $IC_{50}$ value of 1.0 $\mu$M. It further effects maximum inhibition of the aldosterone secretion, stimulated by angiotensin II, of adrenocortical cells of a patient suffering from primary hyperaldosteronism (assay 2) at a concentration of 100 nM.

The invention further relates to the use of the optical antipodes of the above compound, viz. (a) (—)-5-(p-cyanophenyl)-5,6,7,8-tetrahydroimidazo-[1,5-a]pyridine and (b) (+)-5-(p-cyanophenyl)-5,6,7,8-tetrahydroimidazo[1,5-a]pyridine, or of a pharmaceutically acceptable non-toxic acid addition salt thereof, for the treatment of hyperaldosteronism, and to a method of treating hyperaldosteronism using such compounds, and to the use of said compounds for the preparation of pharmaceutical compositions for the treatment of hyperaldosteronism.

Surprisingly, it has been found that the above mentioned (+)-antipode in vitro and in vivo has a much greater specificity than the corresponding racemate.

Accordingly, the present invention relates first and foremost to the use of (+)-5-(p-cyanophenyl)-5,6,7,8-tetrahydroimidazo[1,5-a]pyridine, or of a pharmaceutically acceptable non-toxic acid addition salt thereof, for the treatment of hyperaldosteronism, and to a method of treating hyperaldosteronism using such compounds, and to the use of said compounds for the preparation of pharmaceutical compositions for the treatment of hyperaldosteronism.

As has been stated above, the compounds of formulae I and I*, wherein $R_1$, $R_2$ and n have the above meanings, and pharmaceutically acceptable non-toxic salts thereof, can be used for the preparation of pharmaceutical compositions for the treatment of hyperaldosteronism.

The pharmaceutically acceptable compositions obtainable in the practice of this invention are those for enteral, for example peroral or rectal, also for sublingual as well as parenteral, administration.

Suitable dosage unit forms, especially for peroral and/or sublingual administration, for example dragées, tablets or capsules, contain preferably from ca. 2 mg to 20 mg, most preferably from ca. 2 mg to 10 mg, of one of the above cited compounds or of a pharmaceutically acceptable salt thereof, together with pharmaceutically acceptable carriers. The amount of active ingredient in such pharmaceutical compositions is from ca. 5% to 90%, preferably from ca. 10% to 60%.

Suitable excipients for pharmaceutical compositions for oral administration are in particular fillers such as sugar, for example lactose, saccharose, mannitol or sorbitol, cellulose preparations and/or calcium phosphates, e.g. tricalcium phosphate or calcium hydrogen phosphate, and also binders such as starch pastes, e.g. maize, corn, rice or potato starch, gelatin, tragacanth, methyl cellulose and/or hydroxypropyl cellulose, disintegrators such as the above-mentioned starches, carboxymethyl starch, crosslinked polyvinylpyrrolidone, agar, alginic acid or a salt thereof such as sodium alginate, and/or cellulose, for example in crystalline, especially microcrystalline, form, and/or glidants and lubricants, for example silica, talcum, stearic acid or salts thereof such as magnesium stearate or calcium stearate, cellulose and/or polyethylene glycol.

Dragée cores are provided with suitable coatings which can be resistant to gastric juices, using, for example, concentrated sugar solutions which may contain gum arabic, talcum, polyvinylpyrrolidone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropylmethyl cellulose phthalate.

Further pharmaceutical compositions for oral administration are dry-filled capsules made of gelatin and also soft sealed capsules consisting of gelatin and a plasticiser such as glycerol or sorbitol. The dry-filled capsules may contain the active ingredient in the form of granules, for example in admixture with fillers such as lactose, binders such as starches, and/or glidants such as talcum or magnesium stearate, and, in some cases, with stabilisers. In soft capsules, the active ingredient is preferably dissolved or suspended in a suitable liquid, such as a fatty oil, paraffin oil or a liquid polyethylene glycol, to which a stabiliser and/or bactericide may also be added. It is also possible to use capsules which are readily chewable, so that the sublingual ingestion of the active ingredient can effect as rapid an onset of action as possible.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols. It is also possible to use gelatin rectal capsules which contain a combination of the active ingredient with a base material. Suitable base materials are e.g. liquid triglycerides, polyethylene glycols or paraffin hydrocarbons.

Particularly suitable dosage forms for parenteral administration are aqueous solutions of an active ingredient in water-soluble form, for example a water-soluble salt, and also suspensions of the active ingredient, such as corresponding oily injection suspensions, using suitable lipophilic solvents or vehicles such as fatty oils, for example sesame oil, or synthetic fatty acid esters, for example ethyl oleate or triglycerides, or aqueous injection suspensions which contain substances which increase the viscosity, for example sodium carboxymethyl cellulose, sorbitol and/or dextran, and in some cases also stabilisers.

Dyes or pigments can also be added to the pharmaceutical compositions, especially to the tablet or dragée coatings, for example to identify or indicate different doses of active ingredient.

The pharmaceutical compositions of this invention are prepared in a manner known per se, for example by conventional mixing, granulating, confectioning, dissolving or lyophilising methods. For example, pharmaceutical compositions for oral administration can be obtained by combining the active ingredient with solid carriers, optionally granulating a resulting mixture and processing the mixture or granulate, if desired or necessary after the addition of suitable excipients, to tablets or dragée cores.

The following Examples illustrate the claimed invention in more detail. It is to be emphasised that these Examples are purely illustrative in character and in no way limit the scope of the invention.

EXAMPLE 1

Preparation of 10 000 tablets each containing 10 mg of active ingredient

Composition

| Composition: | |
|---|---|
| 5-(p-cyanophenyl)-5,6,7,8-tetrahydroimidazo[1,5-a]pyridine hydrochloride | 116.33 g |
| lactose | 2535.00 g |
| corn starch | 125.00 g |
| polyethylene glycol 6000 | 150.00 g |
| talcum | 150.00 g |
| magensium stearate | 40.00 g |
| purified water | q.s. |

Procedure

All the powdered constituents are sieved through a sieve having a mesh size of 0.6 mm. The active ingredient is then mixed with lactose, talcum, magnesium stearate and half of the starch in a suitable mixer. The other half of the starch is suspended in 65 ml of water and the suspension is added to a boiling solution of polyethene glycol in 260 ml of water. The resultant paste is added to the powders and granulated, optionally with the further addition of water. The granulate is dried overnight at 35° C., sieved through a sieve having a mesh size of 1.2 mm, and compressed to tablets with a breaking notch.

EXAMPLE 1a

The procedure of Example 1 is repeated, using 116.33 g of (+)-5-(p-cyanophenyl)-5,6,7,8-tetrahydroimidazo[1,5-a]pyridine hydrochloride as active ingredient, to give 10 000 tablets each containing 10 mg of this active ingredient in the form of the free base.

EXAMPLE 2

Soft gelatin capsules containing 20 mg of 5-(p-cyanophenyl)-5,6,7,8-tetrahydroimidazo[1,5-a]pyridine hydrochloride can be prepared by processing 150 mg of a mixture comprising 20.000 mg of 5-(p-cyanophenyl)-5,6,7,8-tetrahydroimidazo[1,5-a]pyridine hydrochloride, 0.075 mg of 2,6-di-tert-butyl-4-methylphenol, 0.015 mg of citric acid, 0.135 mg of 1,2-propylene glycol, 102.775 mg of colza oil, 20.000 mg of soya lecithin and 7.000 mg of wax mixture, by a standard method which is known per se, preferably by the R. P. Scherer method, to a soft gelatin capsule. The capsule shell consists of 0.250 mg of ethyl parabene (ethyl 4-hydroxybenzoate), 0.130 mg of propyl parabene (n-propyl 4-hydroxybenzoate), 25.000 mg of gelatin and 54.600 mg of glycerol.

EXAMPLE 2a

The procedure of Example 2 is repeated, using 20.000 mg of (+)-5-(p-cyanophenyl)-5,6,7,8-tetrahydroimidazo[1,5-a]pyridine hydrochloride as active ingredient, to give soft gelatin capsules each containing 20 mg of this active ingredient.

What is claimed is:

1. A method of treating hyperaldosteronism in a mammal in need thereof comprising administering an effective amount of a compound of formula Ia

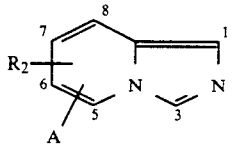

wherein A is $R_1$-phenyl; $R_1$ is lower alkyl, hydroxy-lower alkyl, halogen, amino, formyl, carboxy, lower alkoxycarbonyl, cariamoyl, N-lower alkylcarbamoyl or cyano; and $R_2$ is hydrogen;

or of a compound of formula Ia*

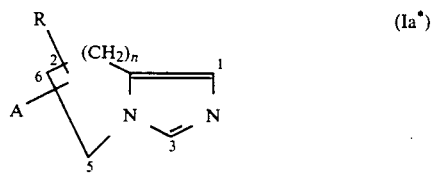

wherein n is 1, 2, or 3; A and $R_1$ are as defined above; and $R_2$ is hydrogen, lower alkylthio, lower alkoxycarbonyl, phenyl-lower alkyl, carboxy-lower alkyl, or lower alkoxycarbonyl-lower alkyl; in a compound of formula Ia* it being possible for A and $R_2$ to be attached to each of the saturated carbon atoms of the saturated ring, either both to the same carbon atom or to different carbon atoms; or of a stereisomer or mixture of stereoisomers thereof or of a pharmaceutically acceptable salt thereof.

2. The method of claim 1 wherein 5-(p-cyanophenyl)-5,6,7,8-tetrahydroimidazo[1,5-a]pyridine or a pharmaceutically acceptable non-toxic acid addition salt thereof, is administered.

3. The method of claim 1 wherein (+)-5-(p-cyanophenyl)-5,6,7,8-tetrahydroimidazo[1,5-a]-pyridine or a pharmaceutically acceptable non-toxic acid addition salt thereof, is administered.

4. The method of claim 1 wherein (−)-5-(p-cyanophenyl)-5,6,7,8-tetrahydroimidazo[1,5-a]-pyridine or a pharmaceutically acceptable non-toxic acid addition salt thereof, is administered.

* * * * *

UNITED STATES PATENT AND TRADEMARK OFFICE
CERTIFICATE OF CORRECTION

PATENT NO. : 5,057,521

DATED : October 15, 1991

INVENTOR(S) : Albert Hausler and Ajay Bhatnagar

It is certified that error appears in the above-identified patent and that said Letters Patent is hereby corrected as shown below:

Column 11, line 30, please delete "cariamoyl" and insert -- carbamoyl-- in lieu thereof.

Signed and Sealed this

Seventh Day of September, 1993

Attest:

BRUCE LEHMAN

Attesting Officer   Commissioner of Patents and Trademarks